United States Patent [19]

Costello et al.

[11] Patent Number: 4,590,308

[45] Date of Patent: May 20, 1986

[54] SELECTIVE HALOGENATION OF BENZENE DI AND TRI-METHANOL COMPOUNDS

[75] Inventors: Alan T. Costello, Ashton-under-Lyne; David J. Milner, Whitefield, both of England

[73] Assignee: Imperial Chemical Industries PLC, London, England

[21] Appl. No.: 694,161

[22] Filed: Jan. 23, 1985

[30] Foreign Application Priority Data

Feb. 10, 1984 [GB] United Kingdom ............... 8403548

[51] Int. Cl.$^4$ ............................................. C07C 33/46
[52] U.S. Cl. .................................................. 568/812
[58] Field of Search ....................... 568/812, 840, 841

[56] References Cited

U.S. PATENT DOCUMENTS 3,714,276 1/1973 Pierce et al. ..................... 568/812
3,899,466 8/1975 Dubecke et al. .................. 568/812

FOREIGN PATENT DOCUMENTS 0015093 of 1914 United Kingdom ............... 568/841

OTHER PUBLICATIONS

OPPI Briefs, 15(1-2), 63-70, (1983), Camp et al.
Org. Syntheses Coll. vol. 3, 446-448 (1955), Campbell et al.
JACS, 72, 5137-5138, (1950) Setliff et al.

*Primary Examiner*—Werren B. Lone
*Attorney, Agent, or Firm*—Cushman, Darby & Cushman

[57] ABSTRACT

Process for the monohalogenation of a benzene compound which has 2 or 3 $CH_2OH$ substituents to obtain a product wherein one of the $CH_2OH$ substituents is monohalogenated which comprises reacting an aqueous solution of the compound with hydrochloric or hydrobromic acid in the presence of a water immiscible organic solvent which is inert to the reactants, the partition coefficient of the compound in the aqueous/organic phases being greater, with respect to the aqueous phase, than the partition coefficient of the product. The novel compounds
4-chloromethyl-2,3,5,6-tetrafluorobenzene methanol
and
4-bromomethyl-2,3,5,6-tetrafluorobenzene methanol
are also disclosed.

6 Claims, No Drawings

SELECTIVE HALOGENATION OF BENZENE DI AND TRI-METHANOL COMPOUNDS

This invention relates to a process for the selective halogenation of benzene di- and tri-methanol compounds. The compounds obtained by the process are useful as chemical intermediates in, for example, the synthesis of pesticidal products. The invention includes certain of the compounds, themselves, which are novel.

According to the present invention there is provided a process for the monohalogenation of a compound of the formula (I):

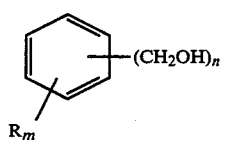

in which R is any substituent other than a substituent that has a significant water solubilising effect on compound (II), as hereinafter defined, or that is halogenated under the conditions of the process, m is zero or an integer of from 1 to 4 and n is 2 or 3, to form a compound of the formula (II):

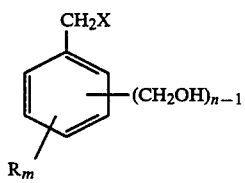

in which X is bromine or chlorine and R, m and n have the meanings already given, which process comprises reacting an aqueous solution of compound (I) with hydrochloric or hydrobomic acid in the presence of a water immiscible organic solvent which is inert to the reactants, the partition coefficient of compound (I) in the aqueous/organic phases being greater, with respect to the aqueous phase, than the partition coefficient of compound (II).

By "partition coefficient" is meant the ratio of the equilibrium concentrations of a substance dissolved in two immiscible solvents. In this case, the partition coefficients of compounds (I) and (II) are the ratios of their equilibrium concentrations in the aqueous phase to their equilibrium concentration in the organic phase.

The water immiscible organic solvent is selected so that sufficient of compound (I) resides in the aqueous phase to undergo halogenation, and compound (II) has a substantially higher preference for the organic phase than compound (I) to avoid over-halogenation. In principle, compound (I) could reside largely in the organic phase provided the partitions of compounds (I) and (II) between the two phases are sufficiently different. Ideally, compound (I) is soluble in the aqueous but not the organic phase and compound (II), vice versa.

The substituent R will also have an effect on the partition coefficients of compounds (I) and (II) and substituents, such as sulphonic acid groups, which will significantly increase the solubility of compound (II) in the aqueous phase should be avoided. Substituents which R may be include alkyl, especially $C_{1-4}$ alkyl, alkoxy, especially $C_{1-4}$ alkoxy, formyl, alkylcarbonyl, especially $C_{1-4}$ alkylcarbonyl, nitro and halogen.

The process of the invention is of particular interest for the monohalogenation of compounds (I) in which n is 2, especially when the hydroxymethyl groups are in positions para to each other, and more especially when $R_m$ is $Cl_4$ or $F_4$. In particular, the process may be used for the preparation of 4-chloromethyl-2,3,5,6-tetrafluorobenzene methanol and 4-bromomethyl-2,3,5,6-tetrafluorobenzene methanol which are novel compounds and form another aspect of the present invention.

The process may be conveniently carried out by mixing together an aqueous solution of compound(I) hydrochloric or hydrobromic acid and the water immiscible solvent and heating them with stirring to a temperature of 70° C. or above, but below 100° C. If preferred, compound (I) may be dissolved in aqueous acid rather than separately in water, and then mixed with the solvent. The mixture is stirred and maintained at the desired temperature until reaction is judged complete, for example, by sampling the aqueous layer at intervals to determine the amount of unreacted compound (I) remaining. The aqueous and organic layers may then be separated, the organic layer dried and the solvent removed by evaporation to obtain the compound (II). Alternatively, a counter-current extraction process may be used, in which compound (II) is continuously extracted as it is formed by solvent passed through the aqueous medium. Such extraction techniques are known and described in, for example, OPPI Briefs, 15(1-2), 63-70 [1983]; Org.Synth.Coll.Vol., 3, 446-8 [1955] and JACS, 72, 5137-8 [1950].

The strength of the aqueous solution of compound (I) is not critical; typically there is about 10% by weight of compound (I) in the total aqueous phase.

The amount of acid used should be in excess of 1 mol and is preferably from 4 to 5 mols of acid per mol of compound (I).

Any solvent having a boiling point above the reaction temperature may be used, provided that it is inert to the reactants and satisfies the requirements with regard to partition coefficients of compounds (I) and (II) as discussed earlier. Toluene is ideal but it is envisaged that other solvents may be used such as xylene, higher boiling petroleum fractions and chlorinated hydrocarbons. When a continuous extraction process is used, the solvent is preferably lighter than water.

The amount of solvent is not critical. Conveniently sufficient is used to obtain about a 10% solution of compound (II) and hence the aqueous and solvent phases will usually be of approximately equal volume.

The starting material, compound (I), may be obtained by reduction of the halide of the corresponding di- or tri-carboxylic acid. A process for preparing 2,3,5,6-tetrafluorobenzene-1,4-dimethanol is described in UK Patent Specification No. 2127013. The corresponding tetrachloro compound may be obtained by reduction of tetrachloroterephthaloyl chloride which is commercially available. When reduction of the acid halide is carried out in a water miscible solvent, e.g. when using $NaBH_4$ in diglyme, the reduction mixture may be used directly in the process of the invention without isolation of the benzene di- or tri-methanol compound.

The compounds (II), obtained by the process of the invention, are useful as chemical intermediates for the synthesis of various products. For example, 4-bromo- and 4-chloromethyl-2,3,5,6-tetrafluorobenzene methanols are precursors of 4-methyl-2,3,5,6-tetrafluorobenzene methanol which is useful in the preparation of pesticidal compounds. In this case, reduction of the 4-bromo- and 4-chloromethyltetrafluorobenzene methanols to the corresponding 4-methyl compound may proceed using the solvent solutions without prior isolation of the 4-bromo- and 4-chloromethyl compounds.

The invention is illustrated by the following two Examples in which percentages are by weight.

EXAMPLE 1

Preparation of 4-chloromethyl-2,3,5,6-tetrafluorobenzene methanol 2,3,5,6-Tetrafluoro-1,4-benzene dimethanol (1 g; 4.8 m.mol) was added to hydrochloric acid 36°Tw (10 ml; 115 m.mol) at 20° C., followed by toluene (10 ml). The mixture was then stirred and warmed to 90° C. and maintained at this temperature for 7 hours to complete the reaction.

The mixture was then cooled and the stirring stopped. After being allowed to settle, the lower aqueous layer was run off. The toluene layer was dried over magnesium sulphate and the solvent removed under reduced pressure to give a pale coloured solid (0.65 g; 60% yield).

The aqueous layer was extracted with ether (2×10 ml), the extracts combined and the ether removed under reduced pressure to give 0.2 g of starting material.

The yield of product in terms of diol consumed was 75%.

EXAMPLE 2

Preparation of 4-bromomethyl-2,3,5,6-tetrafluorobenzene methanol 2,3,5,6-Tetrafluoro-1,4-benzene dimethanol (1 g; 4.8 m.mol) was added to water (5 ml). Hydrobromic acid 48% (5 ml; 47 m.mol) was then added followed by toluene (10 ml). The mixture was stirred and warmed to 85° to 90° C. and maintained at this temperature for 4 hours. The mixture was then cooled, the agitation stopped and the toluene layer separated.

The toluene was dried over magnesium sulphate and removed under reduced pressure to give a cream coloured solid (0.7 g; yield 54%).

The aqueous layer was extracted with ether (2×10 ml) and the ether removed under reduced pressure to give 0.5 g of starting material. The yield of product in terms of material consumed was 100%.

We claim:

1. A process for the monohalogenation of a compound of the formula (I)

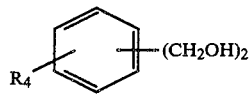

in which each R, which may be the same or different, is fluorine or chlorine to form a compound of the formula (II):

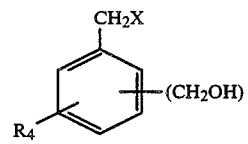

in which X is bromine or chlorine and R has the meaning already given, which process comprises (a) reacting an aqueous solution of compound (I) with hydrochloric or hydrobromic acid in the presence of a water immiscible organic solvent which is inert to the reactants, the partition coefficient of compound (I) in the aqueous/organic phases being greater, with respect to the aqueous phase, than the partition coefficient of compound (II) and (b) separating the aqueous and organic layers and removing the organic solvent to obtain the compound (II).

2. A process according to claim 1 in which the hydroxymethyl groups are in positions para to each other.

3. A process according to claim 1 in which the water immiscible organic solvent is toluene.

4. A process according to claim 1 in which the reaction is carried out at a temperature of from 70° C. to below 100° C.

5. 4-Chloromethyl-2,3,5,6-tetrafluorobenzene methanol.

6. 4-Bromomethyl-2,3,5,6-tetrafluorobenzene methanol.

* * * * *